(12) United States Patent
Keeley

(10) Patent No.: US 8,062,269 B2
(45) Date of Patent: Nov. 22, 2011

(54) FAIL SAFE DUAL CHAMBER PERITONEAL DIALYSIS/INFUSION SYSTEM

(75) Inventor: Robert C. Keeley, Kildeer, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1419 days.

(21) Appl. No.: 11/423,345

(22) Filed: Jun. 9, 2006

(65) Prior Publication Data

US 2007/0287966 A1    Dec. 13, 2007

(51) Int. Cl.
*A61M 5/00* (2006.01)

(52) U.S. Cl. .................................... 604/246; 604/248

(58) Field of Classification Search .................. 604/6.1, 604/9, 29, 30, 32, 33, 43, 82, 83, 84, 85, 604/167.05, 236, 248, 249
See application file for complete search history.

(56) References Cited

U.S. PATENT DOCUMENTS

| | | | |
|---|---|---|---|
| 2,335,085 A * | 11/1943 | Roberts | 137/625.11 |
| 3,276,472 A * | 10/1966 | Jinkens et al. | 137/556 |
| 4,306,705 A | 12/1981 | Svensson | |
| 5,045,068 A | 9/1991 | Kawai et al. | |
| 5,209,347 A | 5/1993 | Fabisiewicz et al. | |
| 5,540,668 A * | 7/1996 | Wilson et al. | 604/248 |
| 6,083,205 A | 7/2000 | Bourne et al. | |
| 6,165,168 A * | 12/2000 | Russo | 604/533 |
| 6,213,334 B1 * | 4/2001 | Coelho et al. | 220/501 |
| 6,485,483 B1 | 11/2002 | Fujii | |
| 6,589,197 B1 | 7/2003 | Doi et al. | |

FOREIGN PATENT DOCUMENTS

| | | |
|---|---|---|
| CA | 2 388 531 | 3/2002 |
| EP | 0 375 681 | 11/1992 |
| EP | 0 715 860 | 6/1996 |
| EP | 1 221 322 | 7/2002 |
| EP | 1 221 323 | 7/2002 |
| EP | 1 234 596 | 8/2002 |
| EP | 0 758 909 | 10/2002 |
| EP | 1 543 862 | 6/2005 |
| WO | WO 93/19808 | 10/1993 |
| WO | WO 93/25262 | 12/1993 |
| WO | WO 95/08299 | 3/1995 |
| WO | WO 96/04039 | 2/1996 |
| WO | WO 96/40359 | 12/1996 |
| WO | WO 99/38558 | 8/1999 |
| WO | WO 00/29061 | 5/2000 |

(Continued)

OTHER PUBLICATIONS

Written Opinion of the International Searching Authority (9 pgs.).

*Primary Examiner* — Christopher D Koharski

(74) *Attorney, Agent, or Firm* — K&L Gates LLP

(57) ABSTRACT

A flow control manifold includes a valve housing having first and second inlets and an outlet. The valve housing defines a cavity sized to slideably engage a valve having a first position and a second position. The flow control manifold may further include a first flow path defined within the valve and a second flow path defined within the valve such that the first flow path fluidly couples the first and second inlets to the outlet along the second flow path when the valve is in the first position.

15 Claims, 5 Drawing Sheets

FOREIGN PATENT DOCUMENTS

| | | |
|---|---|---|
| WO | WO 00/62844 | 10/2000 |
| WO | WO 02/18781 | 3/2002 |
| WO | WO 03/039646 | 5/2003 |
| WO | WO 03/059432 | 7/2003 |
| WO | WO 03/079956 | 10/2003 |
| WO | WO 03/086529 | 10/2003 |
| WO | WO 03/094826 | 11/2003 |
| WO | WO 2004/004806 | 1/2004 |
| WO | WO 2004/022151 | 3/2004 |
| WO | WO 2004/045704 | 6/2004 |
| WO | WO 2004/075972 | 9/2004 |
| WO | WO 2004/082757 | 9/2004 |
| WO | WO 2005/016443 | 2/2005 |
| WO | WO 2005/068011 | 7/2005 |

* cited by examiner

FIG. 3
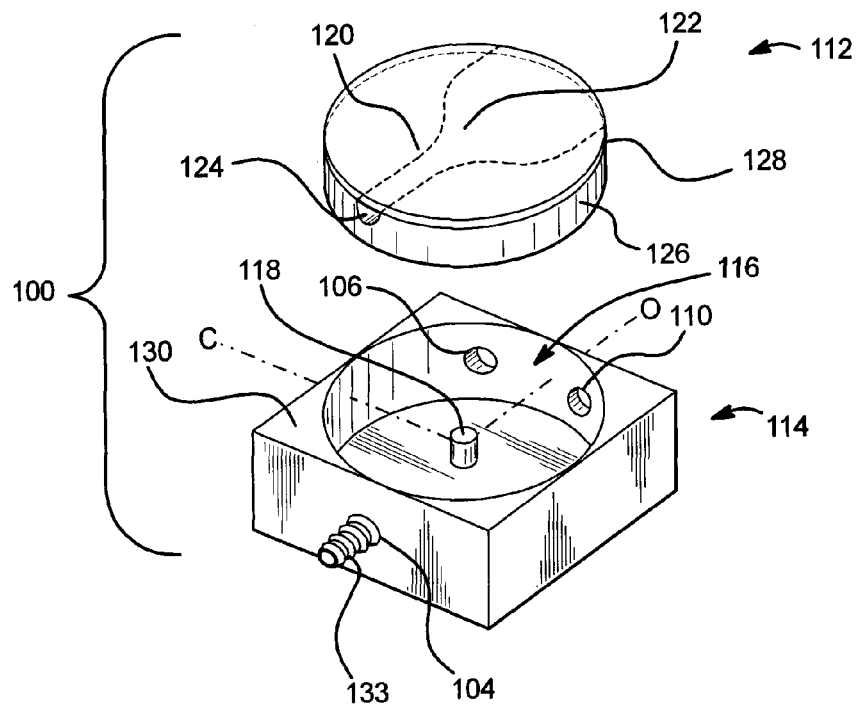
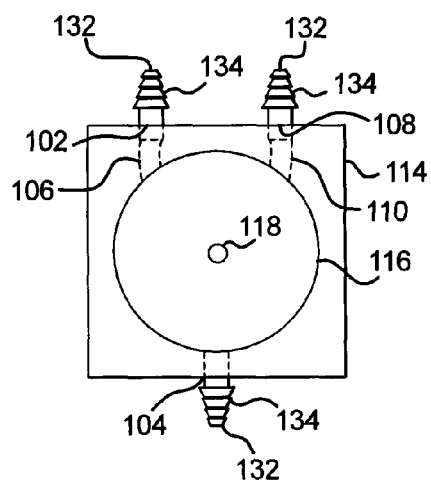
FIG. 4A
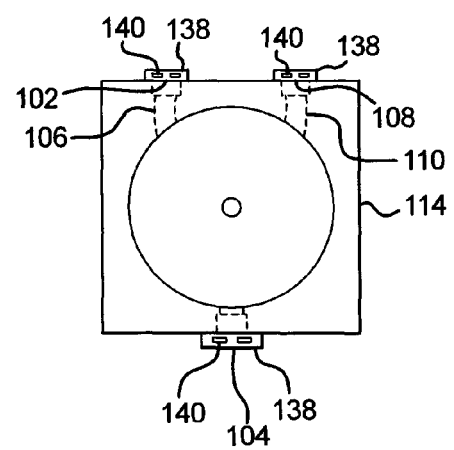
FIG. 4B

FIG. 5A
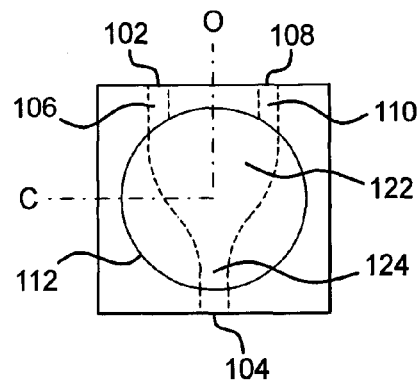
FIG. 5B
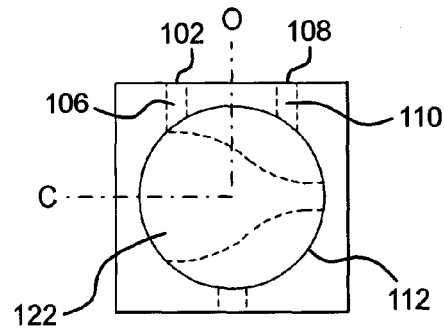
FIG. 6A
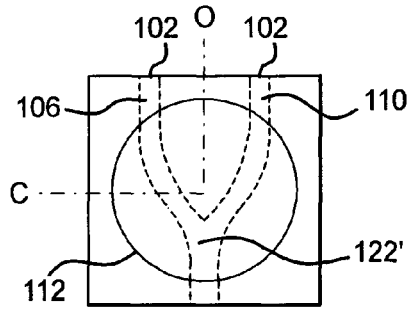
FIG. 6B
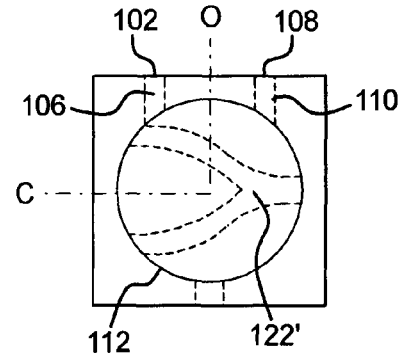
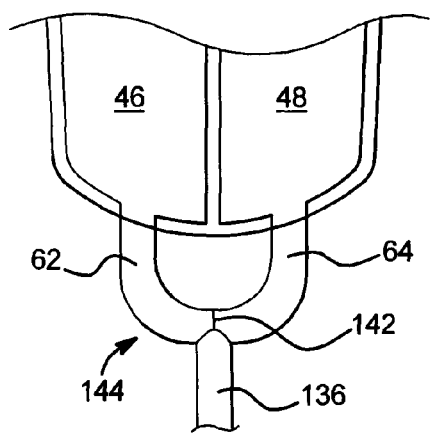
FIG. 7A
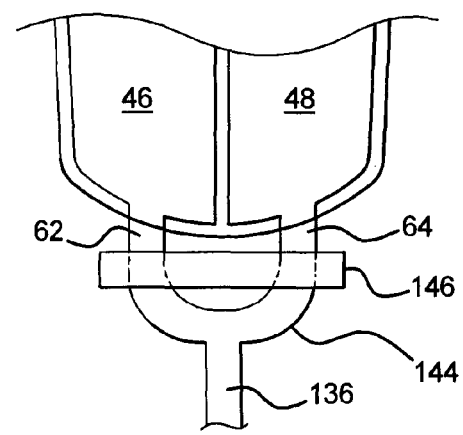
FIG. 7B

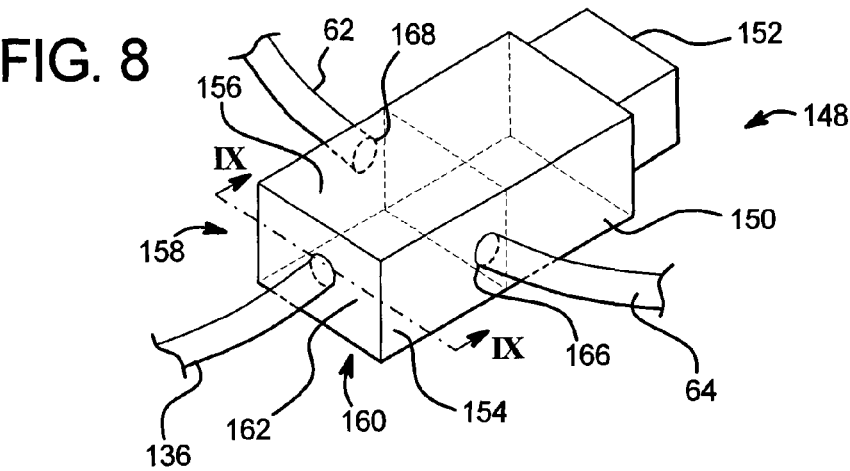
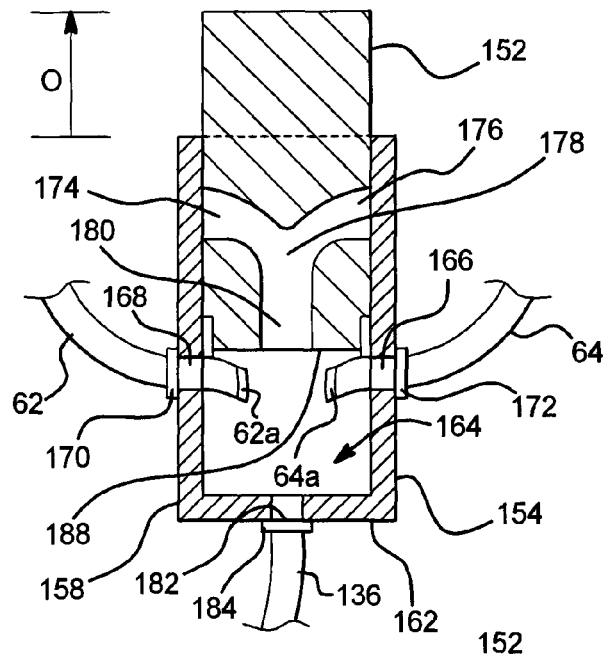
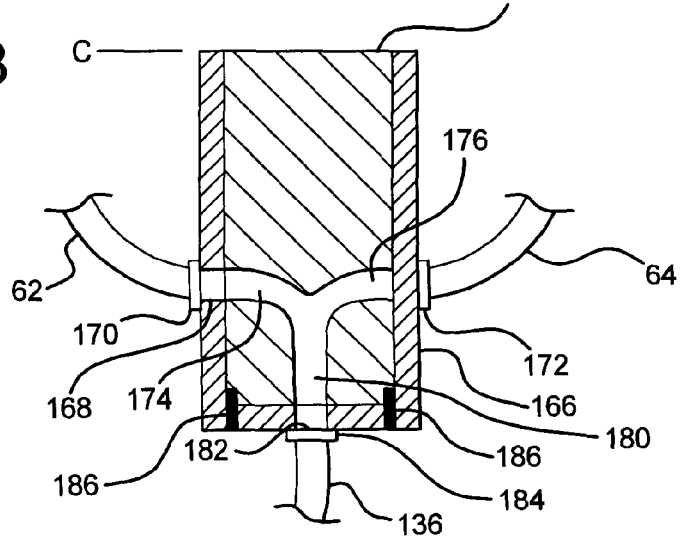

FAIL SAFE DUAL CHAMBER PERITONEAL DIALYSIS/INFUSION SYSTEM

BACKGROUND

Many medical solutions must be separated into their constituent components for storage in order to maintain stability, viability or to satisfy other medical concerns. These solutions may be stored in separate containers, but are often stored in separate chambers of a single container. The chambers of the container and the constituent components of the solution are often separated by a frangible heat seal. One example of such a double or dual chambered container is disclosed in U.S. Pat. No. 5,209,347 which is incorporated herein by reference for all purposes, and which is assigned to the Baxter International Inc., the assignee of the present application. This container includes a frangible seal that permits the mixing and combination of the constituent components of the solution when the seal is broken by hand and fluid pressure against the sides of the bag. Peelable seals are one type of frangible seal commonly utilized to permit the mixing and combination of constituent fluids stored in separate compartments of a dual chambered container via a pulling and/or twisting applied to the opposing sides of the container.

FIG. 1 illustrates one example of a known multiple chamber container 10 having a first and second chambers 12, 14 separated by a peelable seal 16. The container 10 is formed from first and second sheets 18, 20 of polymeric film aligned and registered relative to each other. The first and second sheets 18, 20 are joined or secured along a perimeter bond 22. The peelable seal 16 divides the interior formed by the cooperation of the bonded first and second sheets 18, 20 into the first and second chambers 12, 14.

The peelable seal 16 further divides the container 10 into third chamber 24 sized to support and isolate an access port 26. In particular, the peelable seal 16 includes sub-seal portions 16a, 16b arranged to define the substantially wedge or pie-shaped third chamber 24. The access port 26 is arranged with a first end 26a arranged and isolated within the third chamber 24. The access port 26 body extends through the perimeter bond 22 such that a second end 26b is exposed and accessible external to the container 10. In operation the peelable seal 16 and sub-seal portions 16a, 16b separate the first and second chambers 12, 14 and isolate the access port 26 prior to the combining the constituent components of the solution.

The constituent components of the solution can be combined and dispensed by applying pressure to one or both of the chambers 12, 14 to force the fluid against the peelable seal 16. The fluid force against the peelable seal 16 causes the first and second sheets 18, 20 to separate or peel apart thereby allowing the fluid to mix into solution. Similarly, the fluid force against the sub-seal portions 16a, 16b causes a separation that allows the solution to access the first end 26 a of the access port 26.

It is known that these, and other similar, peelable container systems require a great deal of fluid force to separate the peelable seal 16. The large force requirement can be difficult for individuals having limited upper body strength such as infirmed or elderly patients. Moreover, these container systems provide no system or method for resealing or interrupting fluid flow once the peelable seal 16 has been separated.

While the above description discloses a known system for storing and controlling the constituent components of a solution, a need exists for a simpler, more efficient and/or more flexible system of storing and controlling the constituent components of a solution.

SUMMARY

Illustrative examples of dual chamber containers and fluid control devices are discussed below in the Detailed Description section of this specification. The examples include various embodiments and configurations of fluid control devices and manifolds that include, for example, rotary, linear and frangible control mechanisms.

In particular, one embodiment of a flow control manifold includes a valve housing having first and second inlets and an outlet, and defining an interior or cavity. The manifold further includes a valve sized to slideably engage the cavity and having a first position and a second position. The valve defines a first flow path and a second flow path, wherein the first flow path fluidly couples the first and second inlets to the outlet along the second flow path when the valve is in the first position.

The first flow path and the second flow path can cooperate to define a mixing chamber. Alternatively, the first flow path includes a first inlet path arranged adjacent to the first inlet when the valve is at the first position, and the second flow path includes a second inlet path arranged adjacent to the second inlet when the valve is at the first position.

In another embodiment, the cavity can be a cylindrical cavity configured to rotatably carry the valve. The valve can further include at least one cutting surface arranged adjacent to the first and second inlets.

In another embodiment, the cavity is a substantially linear cavity configured to slideably carry the valve. The valve can be a plunger valve configured to cooperate with the first and second inlets. Moreover, the plunger valve can includes at least one cutting surface arranged adjacent to the first and second inlets.

In another embodiment, the manifold can further include a dual chamber fluid container having first and second access ports each configured to fluidly connect one of the chambers.

In another embodiment, the first and second inlets each carry a sealable septum.

In yet another embodiment, a flow control manifold is disclosed and configured to control the flow of liquids received from first and second access ports fluidly coupled to a dual chamber container. The manifold includes a housing configured to cooperate with the first and second access ports of the dual chamber container, and a valve carried within the housing. The valve configured to rotatably cooperate with the first and second access ports through the housing via a first flow path and a second flow path fluidly coupled to the first flow path when the valve is arranged in a first position. The valve further includes an outlet fluidly coupled to the first and second access ports when the valve is arranged in the first position.

In another alternate embodiment, the first flow path and the second flow path cooperate to define a mixing chamber.

In another alternate embodiment, the first flow path includes a first inlet path configured to cooperate with the first access port when the valve is at the first position and the second flow path includes a second inlet path configured to cooperate with the second access port when the valve is at the first position.

In another alternate embodiments, the housing includes first and second inlets. The first and second inlets each include a sealable septum arranged to cooperate with the first and second access ports of the dual chambered container.

In another embodiment, the valve includes at least one cutting surface arranged adjacent to cooperate with the first and second access ports of the dual chambered container.

In yet another embodiment, a flow control manifold that includes a housing having first and second inlets and an outlet, and a slideable valve sized to cooperate with the first and second inlets and the outlet, the valve having a first position and a second position. The slideable valve includes a first flow path and a second flow path fluidly coupled to the first flow path when the valve is arranged in a first position such that the first flow path fluidly couples the first and second inlets to the outlet along the second flow path when the slideable valve is in the first position.

Additional features and advantages of the present invention are described in, and will be apparent from, the following Detailed Description of the Invention and the figures.

BRIEF DESCRIPTION OF THE FIGURES

FIG. 3. is an exploded perspective view of one example of a flow control manifold.

FIGS. 4A and 4B are plan views of another example of a flow control manifold body shown in FIG. 3.

FIGS. 5A and 5B are plan views of one example of a flow control valve in a first and second positions, respectively.

FIGS. 6A and 6B are plan views of one example of a flow control valve in a first and second positions, respectively.

FIGS. 7A and 7B are plan views of another example of a flow control system.

FIG. 8. is a perspective view of one example of a flow control manifold.

FIGS. 9A and 9B are cross-sectional views of the flow control manifold in first and second positions, respectively, the views are taken along the section line IX-IX.

DETAILED DESCRIPTION

The examples herein generally relate to devices for controlled dispensing of fluids. In particular, they disclose and describe exemplary embodiments of a flow control device configured to deliver fluids from a dual-chambered container.

Figure 1:
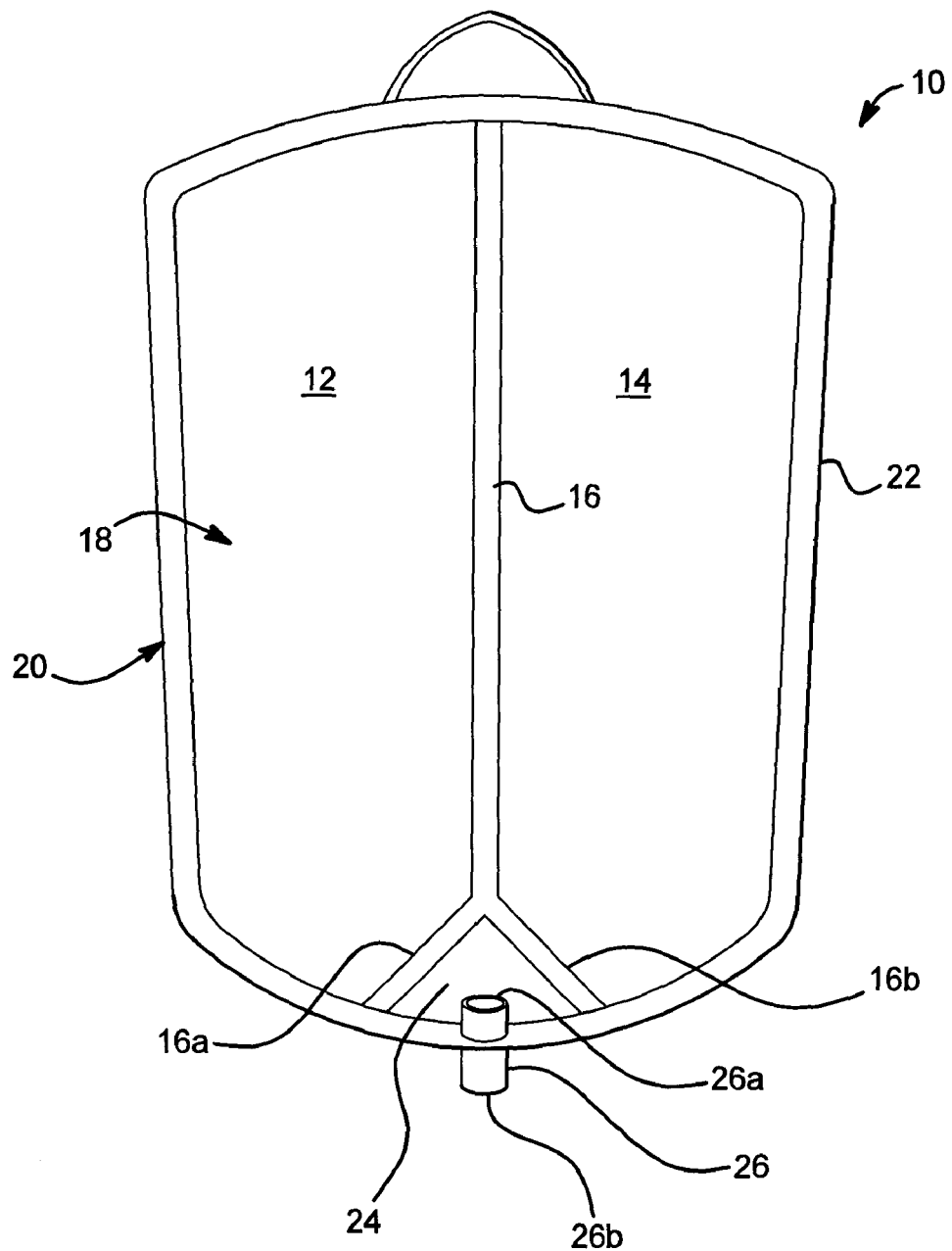
FIG. 1 is a known dual chamber container system.
Figure 2:
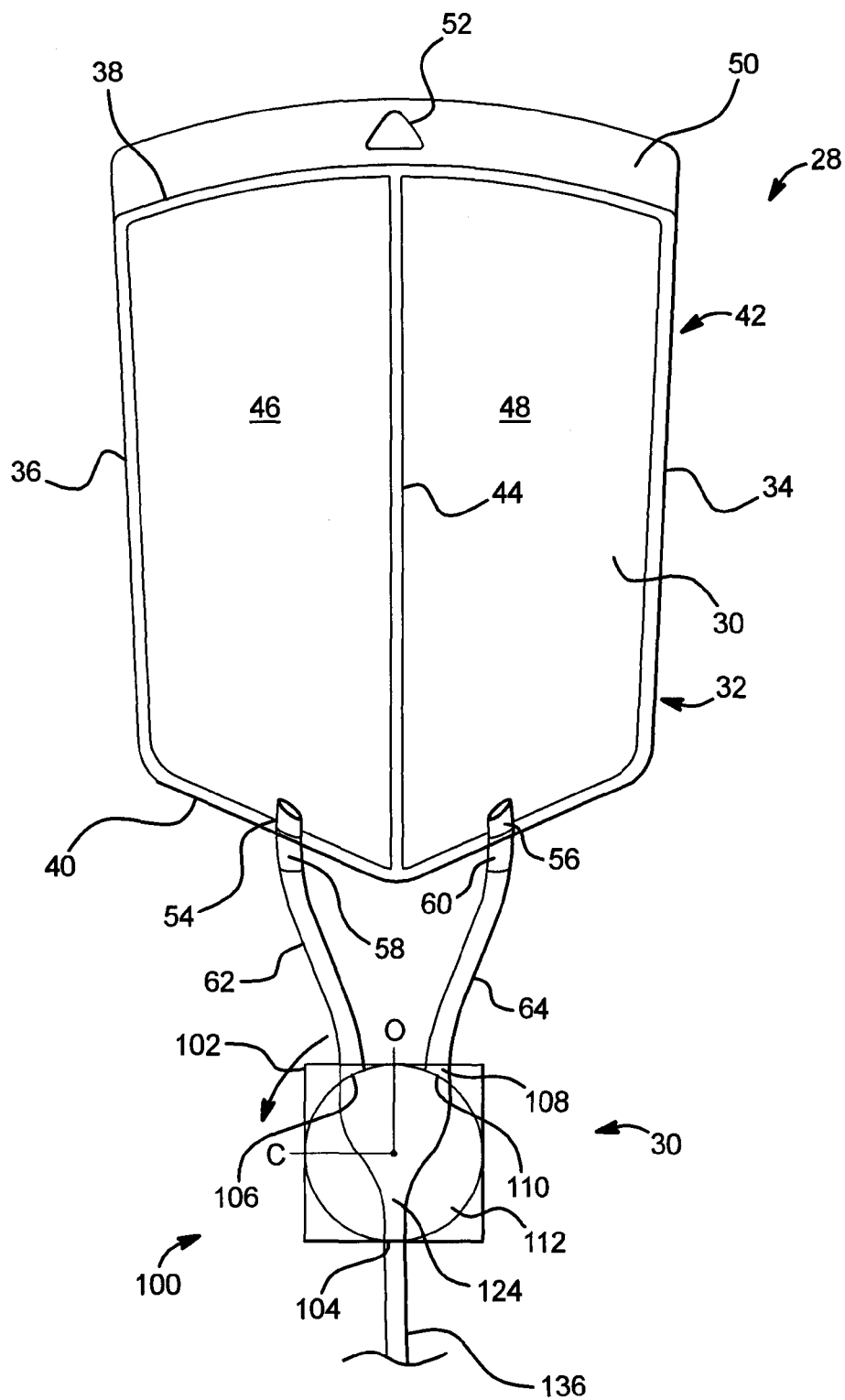
FIG. 2 is one embodiment of a dual chamber container and flow control system constructed in accordance with the disclosure provided herein.

FIG. 2 illustrates one embodiment of a dual chamber container 28 fluidly coupled to a flow control system or manifold 100 constructed in accordance with the disclosure provided herein. The dual chamber container 28, as described above in connection with the prior art FIG. 1, is typically constructed from first and second sheets 30, 32 of a flexible polymeric material registered and aligned relative each other. In one embodiment, the aligned sheets 30, 32 are bonded, joined or otherwise formed into a roughly rectangular shaped bag having a pair of longitudinal edges 34, 36, a support edge 38 and a dispensing edge 40. When aligned, the edges 34, 36, 38, 40 of each of the sheets 30, 32 cooperate and can be joined to define a perimeter bond 42.

The flexible polymeric material of the container 28 and the sheets 30, 32 is generally selected from homopolymers and copolymers of polyolefins, polyamides, polyesters, polybutadiene, styrene and hydrocarbon copolymers, polyimides, polyester-polyethers, polyamide-polyethers to name a few. Alternatively, the flexible polymeric material may be a monolayer material or a multiple layer material. For example, the monolayer material may be produced from a single polymer, and the multilayer material can be a polymer blend that includes specialized layers such as a solution contact layer, a scratch resistant layer, a barrier layer for preventing permeation of oxygen or water vapor, tie layers, or other layers.

The dual chamber container 28 further includes a divider 44 arranged substantially parallel to the longitudinal edges 34, 36. The divider 44 compartmentalizes the container 28 into a first chamber 46 and a second chamber 48. The divider 44 includes portions of the first and second sheets 30, 32 which have been welded or otherwise joined together.

The top edge 38 of the container 28 may define a flap 50 formed by the cooperation of the first and second sheets 30, 32. In particular, the flap 50 is an area of continuously bonded or welded material. The flap 50 may include a cutout or a notch 52 sized or arranged to cooperate with a hook (not shown) to suspend the container 28 during use. Alternatively, the flap 50 could be replaced with a flexible plastic or wire loop (see FIG. 1) that can be used to hang or carry the container 28.

The container 28 includes a pair dispensing apertures 54, 56. Each of the dispensing apertures 54, 56 provides access to one of the first and second chambers 46, 48, respectively. It will be understood that in one embodiment access ports 58, 60 may be secured within the dispensing apertures 54, 56 to control or prevent the flow of fluid within each of the chambers 46, 48. Alternatively, flexible tubes 62, 64 can be secured within the dispensing apertures 54, 56 to provide a flexible, adjustable access to the fluids within the container 28.

In the illustrated embodiment, a flow control valve or manifold 100 is fluidly coupled to the access ports 58, 60 and/or the flexible tubes 62, 64 to provide a fail-safe, user controllable access to the fluids, and ultimately to the solution, stored within the container 28. In the embodiment shown in FIG. 2, the flow control manifold 100 includes a first inlet 102 fluidly coupled to an outlet 104 along a first fluid path 106, and a second inlet 108 fluidly coupled to the outlet 104 along a second fluid path 110. The flow of fluid between the container 28 and the outlet 104 is controlled by a valve 112 that is movable between a closed position C and an open position O, as indicated by the dashed lines oriented approximate ninety degrees (90°) apart.

FIG. 3 illustrates an exploded perspective view of one embodiment of the flow control manifold 100. The flow control manifold 100, as generally described above in connection with FIG. 2, includes the valve 112 and a manifold body 114. The manifold body 114 defines a roughly cylindrical-shaped cavity 116 sized to accept the valve 112. In particular, as shown in this embodiment, the valve 112 is a roughly disc-shaped valve sized to rotate about a spindle 118 between the open position O and the closed position C. As shown, the spindle 118 may be formed or secured as a portion of the planar base of the cylindrical cavity 116 and can engage a complimentary depression or bore (not shown) formed in the underside of the disc-shaped valve 112.

The valve 112 includes a substantially funnel shaped flow-way 120 configured to fluidly connect the first and second inlets 102, 108 to the outlet 104. Specifically, the flow-way 120 includes both the first and second flow paths 106, 110 cooperating to define a mixing chamber 122 in which the constituent components of the solution can be combined and distributed prior to passing through the outlet 104 via an outlet flow path 124. For example, when the valve 112 is aligned or rotated to the open position O, the first and second inlets 102, 108 are in fluid communication with the first and second flow paths 106, 100 and the mixing chamber 122. The fluid within the first and second chambers 46, 48 flows into the flow control manifold 100 and combines in solution before leaving in the manifold 100 via the outlet flow path 124 and the outlet 104. When the valve 112 is positioned at the closed position C, the fluid connection between the inlets 102, 108 and the outlet 104 is disrupted.

The valve 112 could include a seal or gasket 126 wrapped about the cylindrical perimeter of the disc. The gasket 126 could be one or more o-rings, a band-like structure (as shown), or have any other suitable cross-section geometry. The gasket 126 provides a sliding seal between the manifold body 114 and the valve 112 to prevent unwanted leaks. If needed, the gasket 126 defines an apertures to allow fluid or solution to flow through the valve 112.

Similarly, the valve could include a cover 128, which may be manufactured from a clear or translucent material to seal the flow-way 120 against leaks. Alternatively, the cover 128 could be sized to cooperate with the surface 130 of the manifold body 114 and the valve 112 to seal and secure the two components together. Furthermore, the cover 128 could include a knob (not shown) configured to be grasped by a user for rotating the valve 112 between the open and closed positions, or vice versa. In one embodiment, the knob (not shown) can be formed and secured to the valve 112, such that when the manifold 100 is closed, the valve 112 and knob are aligned horizontally. Alternatively when the manifold 100 is open, the valve 112 and knob are vertically aligned in a direction substantially parallel the flow of fluid between container 28 and the outlet 104. It will be understood that the rotational movement of the valve 112 can be manually controlled or, alternatively, can be controlled by an automated fluid dispensing device or system.

FIGS. 4A and 4B illustrate plan views of an alternate embodiment for the manifold body 114 shown in FIG. 3. For example, the manifold body 114 shown in FIG. 4A supports hose barbs or no-slip connectors 132. The no-slip connectors 132 are generally each a tapered, frusto-conical shape connecter, similar to the connector 133 shown in FIG. 3, sized to frictionally engage the inner diameter of the flexible tubes 62, 64 and/or the flexible tube 136 coupled to the outlet port 104. The no-slip connectors 132 include a plurality of steps or ridges 134 that are arranged to allow the inner diameter of a tube to slip or slideably connect thereto, but which resist or impede disconnection of the tube.

FIG. 4B illustrates the manifold body 114 configured to support the alternative flexible connectors 138. The flexible connectors 138 could include a septum portion 140 to flexibly seal the manifold body 114 against dirt or contaminants. As shown in this exemplary embodiment, the flexible connector 138 is positioned within the first and second inlets 102, 108 and the outlet 104. The septum portion 140 of the flexible connectors 138 is sized to engage the outer diameter of the flexible tubes 62, 64 and/or the flexible tube 136 (see FIG. 3). Such that, when the flexible tubes 62, 64 are positioned or forced into the corresponding flexible connectors 138, a fluid-tight seal is established between the outer surface of the tubes and the septum portion 140. In this way, the septum portion 140 seals against the outer surface of the tubes to establish a fluid connection between the containers 28 and the outlet 104.

FIGS. 5A, 5B, 6A and 6B are plan views of alternate embodiments of the valve 112 in the first or open position O or the second or closed position C, respectively. FIG. 5A illustrates the valve 112 in the open position O with the first and second flow paths 106, 110 aligned with the first and second inlets 102, 108. In other words, fluid communication exists between fluids in the first and second chambers 46, 48, the mixing chamber 122 and the outlet 104. FIG. 5B illustrates the valve 112 in the closed position C such that the first and second flow paths 106, 110 are not in fluid communication with the outlet 104.

FIGS. 6A and 6B illustrate another embodiment of the valve 112 wherein the first and second flow paths 106, 110 cooperate to define a V-shaped mixing chamber 122'. FIG. 6A illustrates the valve 112 in the open position O where each of the separated first and second flow paths 106, 110 align with corresponding first and second inlets 102, 108. FIG. 6B illustrates the valve 112 in the closed position C such that the first and second flow paths 106, 110 are arranged 90° away from the first and second inlets 102, 108 and are not in fluid communication with the outlet 104.

FIGS. 7A and 7B illustrate plan views of other examples of flow control systems that can be incorporated into the container 28. In particular, the flexible tubes 62, 64, in one embodiment, are connected to form a U-shaped structure 144, which is connected to the flexible tube 136 to form a roughly T-shaped fluid path. FIG. 7A illustrates one exemplary U-shaped structure 144 that includes a frangible or breakable seal 142 positioned to separate the fluid stored within the first and second chambers 46, 48. In particular, the fluid within the first and second chambers 46, 48 is in fluid contact with the frangible seal 142. The frangible seal 142 of the present example is a roughly Y-shaped seal positioned to at the junction of the U-shaped structure 144 and the flexible tube 136 to prevent the flow of fluid there through. It will be understood that the frangible seal 142 could produced in any configuration that prevents the premature mixture and dispensing of the fluids stored within the chambers 46, 48. Alternatively, multiple frangible seals 142 could be employed through the U-shaped structure 144 to control the fluid flow. Regardless of the seal geometry, when the frangible seal 142 is broken, the fluid within the chambers 46, 48 mixes and flows into the flexible tube 136 for dispensing.

FIG. 7B illustrates another U-shaped structure 144 communicatively connected to the flexible tube 136. In this exemplary embodiment, flow through the U-shaped structure 144 can be disrupted by the presence of a sealing clip 146 attached to an external surface of the structure 144 to prevent unwanted flow between the flexible tubes 62, 64 and the flexible tube 136. In particular, the sealing clip 146 can be removably attached to the flexible tubes 62, 64 to clamp down and prevent the flow of liquid there through. Upon removal of the sealing clip 146, the fluid within the chambers 46, 48 is allowed to mix and flow to the flexible tube 136.

FIGS. 8, 9A and 9B illustrate another embodiment of a linear flow control manifold 148. The linear flow control manifold 148 includes a manifold or flow control body 150 sized to slideably accept a valve or plunger 152 translatable and adjustable by user actuation. The manifold body 150, in this exemplary embodiment, is a substantially rectangular structure having four side walls 154, 156, 158 and 160, and an end wall 162. The four side walls 154, 156, 158 and 160 and the base wall 162 cooperates to define a substantially hollow rectilinear interior 164 sized to support the plunger 152 as it translates from the first, open position (see FIG. 9A) to the second, closed position (see FIG. 9B) and vice versa. The body 150 and the plunger 152, in an alternate embodiment, can be configured as cylindrical structures. The end wall 162 includes an outlet 182 aligned with a septum 184 and configured to be sealingly connected to the flexible tube 136. The septum 184 is shown adhered to or integrally formed with the end wall 162. Alternatively, the septum 184 can be carried within the outlet 182.

The side wall 154 further includes an inlet 166 sized to carry the flexible tube 64 extending from the chamber 48 of the container 28. Similarly, the side wall 158 includes an inlet 168 sized to carry the flexible tube 62 extending from the chamber 46 of the container 28. The inlets 166 and 168 can support flexible connectors or septums 170, 172, respectively, sized to sealingly engage the ends of the flexible tubes 62, 64. In operation an end 62a of the flexible tube 62 can be inserted through and sealed against the flexible membrane of the septum 170, and an end 64a of the flexible tube 64 can be inserted through and sealed against the flexible membrane of the septum 172 to form fluid connections therebetween.

The plunger 152 includes first and second flow paths 174, 176 arranged to define a mixing chamber 178. The first and second flow paths 174, 176 and the mixing chamber 178 provide a fluid connection to an outlet flow path 180 and the outlet 182 when the plunger 152 is in the second, closed position. For example, the flexible tubes 62, 64 can be positioned within the inlets 166, 168, respectively, when the plunger 152 is in the first, open position, e.g., when the plunger is extended away from the manifold body 150. By translating the plunger 152 to the closed position, e.g., when the plunger is positioned substantially within the manifold body 150, the ends 62a, 64a of the flexible tubes 62, 64 can be brought into fluid communication with the flow paths 174, 176 and the outlet 182. In this way, fluid can be directed and controlled from the chambers 46, 48 of the container 28 into solution and provided to a patient via the outlet flow path 180 and the outlet 182.

The plunger 152 could further include cutter blades 186 secured along a leading edge 188. The cutters 186 can be configured to clip or remove the ends 62a, 64a of the flexible tubes 62, 64 to begin fluid flowing between the container 28 and the outlet 182. It will be understood that at least one the cutter 186 could be incorporated into the valve 112 such that the rotary motion between the open and closed positions swipes and/or clips the flexible tubes 62, 64 to open the container 28.

Alternatively, the plunger 152 could be configured to block the flow of fluid from the chambers 46, 48 when positioned in the second, closed position. For example, the plunger 152 could be a solid member, e.g., devoid of fluid flow paths 174, 178 and 180, that prevents fluid communication in closed position C. In this example, when a user linearly translates the plunger 152 to the open position O, the block is removed and fluid is allowed to flow into the interior which is now the mixing chamber 164 and ultimately to the outlet 182 and septum 184.

Further alternatively, the plunger 152 may define or be attached to a port located to the outlet 182 of the outlet flow path 180. The port may be sized and configured to pierce septum 184 to establish fluid communication with the flexible tube 136 when plunger 152 is in the closed position with respect to the manifold body 150.

Flow control manifolds constructed in accordance with the teaching disclosed herein provide a controllable, fail-safe method of mixing and combining fluids contained within a dual chamber container. Moreover, the disclosed flow control manifolds provide a user-friendly means of initiating and terminating fluid flow using a robust design that is compatible with existing container designs and systems.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A dialysis infusion system comprising:
   a dual chamber fluid container having first and second access ports, each configured to fluidly connect to one of the chambers;
   a manifold body defining a cavity, the manifold body including first and second inlets and an outlet, wherein the first inlet fluidly connects to the first access port and the second inlet fluidly connects to the second access port, the manifold body defining a cavity; and
   a valve sized to slideably engage the cavity, the valve having a first position and a second position, the valve defining a substantially funnel shaped flow-way configured to fluidly connect the first and second inlets to the outlet, the funnel shaped flow-way including a mixing chamber and an outlet flow path, wherein the mixing chamber fluidly couples the first and second inlets to the outlet along the outlet flow path when the valve is in the first position.

2. The system of claim 1, wherein the cavity is a cylindrical cavity configured to rotatably carry the valve.

3. The system of claim 2, wherein the valve includes at least one cutting surface arranged adjacent to at least one of the first and second inlets.

4. The system of claim 1, wherein the cavity is a substantially linear cavity configured to slideably carry the valve.

5. The system of claim 4, wherein the valve is a plunger valve configured to cooperate with the first and second inlets.

6. The system of claim 5, wherein the plunger valve includes at least one cutting surface arranged adjacent to the first and second inlets.

7. The system of claim 1, wherein the first and second inlets each carry a sealable septum.

8. A dialysis infusion system configured to control the flow of liquids received from first and second access ports fluidly coupled to a dual chamber container, the infusion system comprising:
   a body including first and second inlets and an outlet and configured to cooperate with the first and second access ports of the dual chamber container; and
   a valve carried within the body, the valve configured to rotatably cooperate with the first and second access ports through the housing, the valve defining a substantially funnel shaped flow-way configured to fluidly connect the first and second inlets to the outlet, the funnel shaped flow-way including a mixing chamber and an outlet flow path, wherein the mixing chamber fluidly couples the first and second inlets to the outlet along the outlet flow path when the valve is arranged in a first position.

9. The system of claim 8, wherein the housing includes first and second inlets.

10. The system of claim 9, wherein the first and second inlets each include a sealable septum arranged to cooperate with the first and second access ports of the dual chambered container.

11. The system of claim 9, wherein the valve includes at least one cutting surface arranged adjacent to cooperate with the first and second access ports of the dual chambered container.

12. A dialysis infusion system comprising:
   a dual chamber fluid container having first and second access ports each configured to fluidly connect to one of the chambers;

a body having an outlet and a first inlet fluidly connected to the first access port and a second inlet fluidly connected to the second access port; and a slideable valve sized to cooperate with the first and second inlets and the outlet, the valve having a first position and a second position, the slideable valve defining a substantially funnel shaped flow-way configured to fluidly connect the first and second inlets to the outlet, the funnel shaped flow-way including a mixing chamber and an outlet flow path, wherein the mixing chamber fluidly couples the first and second inlets to the outlet along the outlet flow path when the slideable valve is in the first position.

13. The system of claim 12, wherein the slideable valve includes at least one cutting surface arranged adjacent to the first and second inlets.

14. The system of claim 12, wherein the slideable valve is a plunger valve configured to cooperate with the first and second inlets.

15. The system of claim 12, wherein the first and second inlets each include a sealable septum arranged to cooperate with the first and second access ports of the dual chambered container.

* * * * *